United States Patent [19]

Davies

[11] 4,027,972

[45] June 7, 1977

[54] GAS ANALYZER METHOD AND APPARATUS

[75] Inventor: Donald W. Davies, Tujunga, Calif.

[73] Assignee: Andros Incorporated, Berkeley, Calif.

[22] Filed: Mar. 31, 1976

[21] Appl. No.: 672,058

[52] U.S. Cl. .................................. 356/51; 250/343
[51] Int. Cl.² .................... G01J 1/00; G01N 21/24; G01N 21/26; G01N 21/34
[58] Field of Search ............. 356/51; 250/343, 351, 250/373

[56] References Cited

UNITED STATES PATENTS

| | | | |
|---|---|---|---|
| 2,806,957 | 9/1957 | McDonald | 250/351 X |
| 3,005,097 | 10/1961 | Hummel | 250/343 X |
| 3,679,899 | 7/1972 | Dimeff | 250/343 |
| 3,728,540 | 4/1973 | Todd et al. | 250/343 |
| 3,899,252 | 8/1975 | Dimeff | 250/343 |

*Primary Examiner*—Alfred E. Smith
*Assistant Examiner*—T. N. Grigsby
*Attorney, Agent, or Firm*—Fitch, Even, Tabin & Luedeka

[57] ABSTRACT

A method and apparatus are described for determining relative amounts of first and second gases in an unknown mixture of gases. Radiant energy is directed serially through reference volumes of the first and second gases and a volume of the unknown gas. The absorption of the radiant energy by the respective gas volumes is varied at different frequencies. The amount of radiant energy passing through the respective gas volumes is detected and a signal is developed representative of the ratio of the amounts of the first and second gases.

18 Claims, 1 Drawing Figure

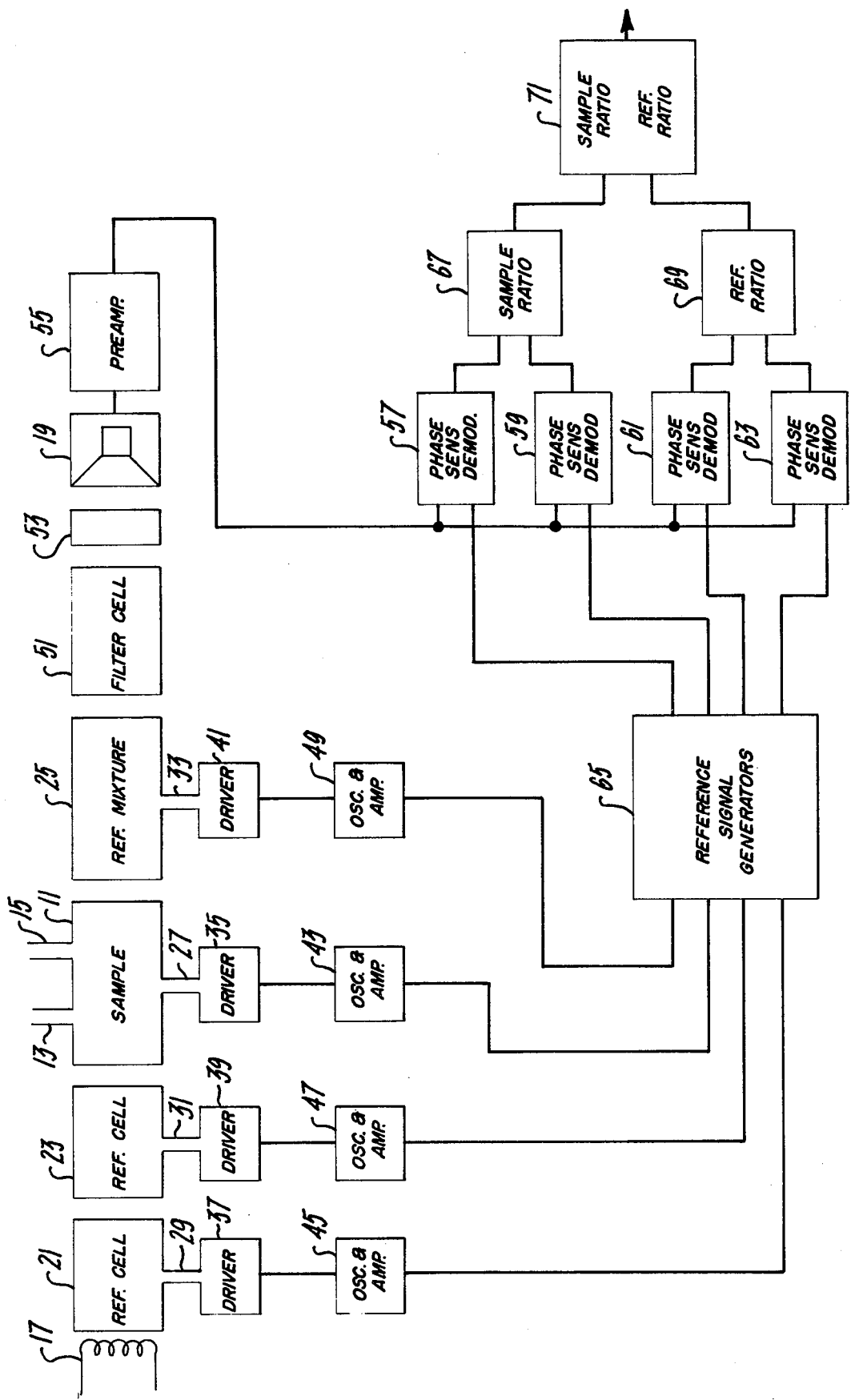

GAS ANALYZER METHOD AND APPARATUS

This invention relates generally to a method and apparatus for analyzing gases. More particularly, the invention relates to an improved method and apparatus for determining the relative amounts of two different gases in an unknown gas mixture.

Nondispersive gas analysis techniques are well known in the prior art. One type of such apparatus which may be employed for determining the presence or absence of a known gas in an unknown gas mixture and the amount of the known gas in the unknown gas mixture is shown and described in U.S. Pat. No. 3,679,899 issued July 25, 1972, Dimeff. The technique described in the aforementioned patent involves the passing of radiation serially through a reference cell containing a known gas and a sample cell containing an unknown gas. The absorption of the radiant energy at a characteristic absorption wavelength band by gas contained in each of the cells is varied. This may be accomplished, for example, by means of varying the density of the gases in the cells or by varying the length of the path taken by the radiant energy in each of the cells. The frequency of the variation accorded to the energy absorption in each of the cells is different from that of the others. The energy passing through the cells is then detected and signals at each of the two frequencies are developed.

If the gas present in the reference cell is not present in the unknown gas mixture, any absorption occurring will be at different wavelengths and the total radiation absorbed will be the sum of the radiation absorbed by the reference cell and the sample cell. On the other hand, if the gas present in the reference cell is also present in the sample cell, both cells will result in the absorption of radiation in the same regions of the wavelength spectrum. In this case, the fraction of the radiation transmitted by both cells will be the product of the respective fractions transmitted by each cell.

If, as previously mentioned, the amount of absorption of energy in the two cells is varied at different frequencies, the amount of light falling on the detector will also vary with time. A Fourier analysis of the signal output of the detector will show large components at the two frequencies at which absorption is varied. If, and only if, the gas present in the reference cell is also present in the unknown gas mixture, side band signals comprising the sum and difference of the two frequencies will also be present. Thus, the heterodyning of the two signals results in an output which may be related to the amount of the type of gas in the reference cell which is present in the sample cell.

In the foregoing described apparatus, if it is desired to analyze the unknown gas mixture for the presence and amount of several different gases, the type of gas in the reference cell must be changed. Although such a procedure may be acceptable for some purposes, there are certain situations in which such a procedure would be cumbersome and unwieldy.

For example, a technique capable of accurately measuring small changes in the relative amounts of carbon 13 and carbon 12 in the carbon dioxide of expired human breath can be of significant benefit in connection with many metabolic studies. The measurement of constituents of the breath under such circumstances is most meaningful if done at periodic intervals and requires careful collection procedures for accuracy. Thus, it is not only more convenient but may, for accuracy, be necessary to measure the relative amounts of the two carbon isotopes simultaneously.

Accordingly, a specific object of the invention is to provide a method and apparatus capable of accurately measuring small changes in enrichment over the naturally occurring level of carbon 13 in gaseous carbon dioxide.

A more general object of the invention is to provide an improved method and apparatus for determining the relative amounts of two known gases in an unknown gas mixture.

A further object of the invention is to provide a method and apparatus for gas analysis which is highly accurate and stable.

Other objects of the invention will become apparent to those skilled in the art from the following description taken in connection with the accompanying drawing wherein the sole FIGURE is a schematic diagram of apparatus constructed in accordance with the invention.

Very generally, the invention pertains to the analysis of gas by providing respective quantities of a first reference gas, a second reference gas, and an unknown gas mixture. Radiant energy is directed serially through the first and second reference gases and the unknown gas mixtures. The radiant energy has a wavelength spectrum which includes the characteristic absorption wavelength of the first and second reference gases. The absorption of the radiant energy by the first and second reference gases and the unknown gas mixture are modulated at three different frequencies such as by modulating the gas density. The amount of radiant energy passing through the two reference gases and the sample gas mixture is detected and processed to provide the desired output.

Referring now more particularly to the drawing, the method of the invention will best be understood by a description of the construction and operation of the illustrated apparatus. As illustrated, the unknown gas mixture is contained in a sample cell 11 having an inlet port 13 and an outlet port 15. The sample cell is disposed in the path of radiant energy emitted from a source 17 and directed to a detector 19. The radiant energy source 17 comprises an infrared source which emits infrared energy having a wavelength spectrum sufficiently broad as to encompass the characteristic absorption wavelengths of the two gases of interest.

Also interposed in the path of radiant energy between the energy source 17 and the detector 19 are first, second and third reference cells 21, 23 and 25, respectively. The reference cell 21 is for containing one of the gases of interest and the reference cell 23 is for containing the other of the gases of interest. The reference cell 25 contains a mixture of the two gases of interest in a predetermined ratio of amounts. This predetermined ratio is selected so as to provide a reference or standard against which the deviation of the relative concentrations in the sample cell 11 is measured. Typically, this ratio will be at or very near the naturally occurring proportions of the mixture.

Each of the cells 11, 21, 23, and 25 is provided with a port 27, 29, 31, and 33, respectively. An acoustic driver, 35, 37, 39 and 41, is attached to each of the ports 27, 29, 31, and 33, respectively. The acoustic drivers may be, for example, typical loudspeakers and may be operated to vary the volume of the cells with which they are associated to cause a variation in the density of the gas or gases contained therein.

Each of the acoustic drivers 35, 37, 39, and 41 is driven by a respective oscillator and power amplifier system 43, 45, 47, and 49 of suitable known construction. The frequencies at which the various acoustic drivers are driven are different, for reasons which will be explained below.

The detector 19 receives radiant energy signals from the source 17 after the energy passes serially through the various cells described above. In addition to the previously named cells, a filter cell 51 is disposed in the path of the radiant energy, and an interface filter 53 is also positioned in the energy path just prior to the detector 19. The interference filter is chosen to select only that portion of the radiation which includes the characteristic absorption wavelength bands of the two gases of interest.

Output signals from the detector, which may be a lead-selenide detector or, if higher sensitivity is required, which may be a liquid nitrogen cooled indium-antimonide detector, are amplified in a preamplifier 55 and applied to each of a series of phase sensitive demodulators 57, 59, 61 and 63. The demodulators 57, 59, 61 and 63 may be of any type suitable for the function subsequently described. Commercially available instruments which are satisfactory include the "Two Phase Vector Lock-In Amplifier", Model 129A, available from Princeton Applied Research Corp., Princeton, New Jersey, and the Dynatrac Model 393 available from Ithaco, Ithaca, New York. Also providing input to the phase sensitive demodulators is a bank 65 of reference signal generators, each of which applies an appropriate sideband signal to a respective one of the phase sensitive demodulators. Each sideband signal frequency thus applied corresponds to the sideband signal frequency being selected by that particular demodulator.

The outputs of the demodulators 57 and 59 are applied to a divider 67. The outputs of the demodulators 61 and 63 are applied to a divider 69. The dividers may be of any suitable construction known in the art and may be digital or analog devices. As will be explained, the output of the divider 67 is a first intermediate signal representative of the ratio of the amounts of each of the gases being analyzed for in the sample. As will also be explained, the output of the divider 69 is a second intermediate signal representative of the amounts of each of the gases being analyzed for in the reference cell 25. These signals are applied to a further divider 71 which develops an output signal representative of the ratio of the two intermediate signals.

For the purpose of promoting a better understanding of the invention, the illustrated apparatus will be described first as operating in a mode in which the third reference cell 25 and its associated elements, the phase sensitive demodulators 61 and 63, the divider 69 and the divider 71 are not active. If the frequency at which the acoustic driver 37 operates is $f_1$, the frequency at which the acoustic driver 35 operates is $f_2$ and the frequency at which the acoustic driver 39 operates is $f_3$; and if the gases contained in the reference cells 21 and 23 are both present in the sample cell 11; signals will be present in the detector output at frequencies $f_1 + f_2$, $f_1 - f_2$, $f_3 + f_2$, and $f_3 - f_2$. It should be noted that heterodyning, that is the production of these sum and difference frequencies, occurs only if the gases in the first and second reference cells are present in the sample.

By using phase sensitive demodulators 57 and 59, that portion of the output signal from the preamp 55 may be selected corresponding to the sideband signals, such as the difference of the frequencies $f_1$ and $f_2$ in the demodulator 57, and $f_3$ and $f_2$ in the demodulator 59. The sum signals or the difference signals are then applied to the divider 67. The output of the divider 67 is therefore a signal representinhg the ratio of the two gases of interest in the sample.

Under the ideal circumstances, where variations in spectral response, pressure excursions, gas concentrations, or other factors are nonexistent or negligible, the simplified system just described provides an accurate representation of the ratio of gases in the sample. The previously mentioned variations, however, are likely to occur in most practical systems. Problems caused by such variations may be avoided by employing the reference cell 25 which includes a standard known ratio of the gases of interest, for example, the naturally occurring ratio. By modulating the absorption of the cell 25 as well, the signals may be processed in any suitable manner to derive an output which represents the ratio of the ratio of the amounts of the two gases in the sample cell to the ratio of the amounts of the two gases in the reference cell 25. In doing so, the effects of most or all of the above mentioned variations may be cancelled out.

The drawing illustrates one form of signal processing wherein the reference cell 25 is used. A second ratioing channel includes the demodulators 61 and 63 and the divider 69. In the demodulator 61 a sideband of the signals at the frequencies $f_1$ and $f_4$ is developed, the frequency $f_4$ being the frequency of the acoustic driver 41. Similarly, the demodulator 63 develops a corresponding sideband of the signals $f_3$ and $f_4$. The corresponding sideband signals, for example the sum or difference signals, are then provided to the divider 69. The resultant output of the divider 69 is a ratio of the concentration of the two gases of interest in the reference mixture contained in the cell 25.

By applying the output of the dividers 67 and 69 to a further divider 71, a ratio of the output signals of the dividers 67 and 69 is obtained which consists of an ultimate ratio of the two ratios. Thus, not only is the concentration of two different gases measurable simultaneously, but by taking the ultimate ratio as above described, the instrument is insensitive to changes in overall gas concentration, changes in transmission of the windows of the cells, pressure excursions, filter characteristics, detector response characteristics, preamplifier gain, or fluctuations in the power of the radiant energy source. This is because all of these variables affect each signal in the same way, leaving the ultimate ratio unaffected.

Typically, the ratio of gases in the reference mixture cell 25 is selected to be relatively close to the expected ratios in the sample cell. The further apart the ratios, the more likelihood there is of non-linearity problems. Optical density in the cells should also be kept relatively close to avoid interferences and other second order effects.

Where the concentration of one of the gases relative to the other is large, problems with non-linearity may result as a consequence of saturation. By placing a filter cell 51 in series, sufficient attenuation is provided to bring both signal to a reasonably close level, making signal processing simpler.

With specific reference to the use of the method and apparatus of the invention in connection with carbon dioxide in exhaled breath, the invention will be described in connection with analyzing the relative amounts of carbon dioxide containing carbon 12 atoms and carbon 13 atoms. Carbon dioxide in expired human breath results from the sum total of all metabolic processes in the body. For many years, the radioactive species carbon 14 and carbon 11 have been used to label a particular substance and the expired carbon dioxide has then been analyzed for the amount of radioactive carbon. Such radioactive species, however, have disadvantages in that the body is exposed to a radiation hazard.

The strongest of the three known absorption bands of carbon dioxide is centered at about 4.3 microns wavelength. This band actually consists of two parts, a band due to carbon 12 and a similar band due to carbon 13 which is shifted to longer wavelengths because of the larger mass of carbon 13 atoms. The carbon 13 band is generally of significantly lower amplitude than the carbon 12 band in natural circumstances but is higher, of course, when the carbon 13 quantities are enriched.

In operating the invention, the cell 21 is filled with carbon dioxide having carbon 13 atoms, the cell 23 is filled with carbon dioxide having carbon 12 atoms, and the cell 25 is filled with a mixture of carbon dioxide containing each of the two isotopes in naturally occuring abundances. The filter cell 51 may be filled with carbon dioxide having substantially only carbon 12 atoms. Since some interference may occur as a result of the presence of carbon 12 in the carbon 13 cell and vice versa, it may be useful to employ a servo system, not shown, to maintain the optical density in the sample cell close to that of the reference cells.

Under these circumstances the instrument operates to take the ratio of the carbon 12 signal to the carbon 13 signal in the sample and the similar ratio in the reference mixture in the cell 25. By dividing the two ratios, the output is directly proportional to the enrichment of the carbon 13 carbon dioxide fraction starting at unity and increasing [decreasing] with carbon 13 enrichment [depletion] in the sample cell.

The gas analyzer constructed in accordance with the invention is capable of achieving an accuracy in the ultimate ratio of one part in $10^3$ or even as much as one part in $10^5$. Because of the double ratioing technique, the apparatus is extremely stable and even with the single ratio technique, drifts of less than 0.1 percent in 24 hours may be expected. The apparatus and technique of the invention is substantially insensitive to interference by other gases present in the sample cell, since the likelihood of overlap is low and even when it occurs, a signal will not be produced unless there is an overlap of individual absorption spectrum lines. Finally, the device may be constructed so that no skilled technician is necessary for its operation.

It may be seen, therefore, that the invention provides a nondispersive heterodyning type of infrared gas analyzer with high sensitivity and selectivity and which is particularly suited to the measurement of the isotopic concentrations of gases such as carbon dioxide. Thus, the instrument is particularly applicable to metabolic studies wherein analysis of expired breath or combusted samples of, for example, blood, spinal fluid, urine, or tissue, is useful. The invention, of course, is also applicable to gas analysis other than in connection with metabolic studies.

Various modifications of the invention in addition to those shown and described herein will become apparent to those skilled in the art from the foregoing description and accompanying drawing. Such modifications are intended to fall within the scope of the appended claims.

What is claimed is:
1. A method for determining the relative amounts of first and second gases in an unknown mixture of gases, comprising, directing radiant energy serially through a first reference volume of said first gas, a second reference volume of said second gas, and a sample volume of the unknown gas mixture, said radiant energy having a wavelength spectrum including characteristic absorption wavelengths of said first and second gases, modulating the absorption of the radiant energy by the first and second reference volumes and the sample volume at first, second, and third frequencies, respectively, detecting the amount of radiant energy passing serially through the first and second reference volumes and the sample volume, developing first and second corresponding sideband signals resulting from heterodyning of the energy modulated at the first and third frequencies and at the second and third frequencies, respectively, and obtaining a ratio of said first and second sideband signals.

2. The method of claim 1 wherein the modulation of the absorption of the radiant energy in the first and second reference volumes and the sample volume is effected by varying the density of the gas in each of said volumes.

3. A method according to claim 1 wherein the path of the serially directed radiant energy includes a third reference volume containing a predetermined ratio of said first and second gases, wherein the absorption of the radiant energy by the third reference volume is modulated at a fourth frequency, wherein are developed third and fourth corresponding sideband signals resulting from heterodyning of the radiant energy at the first and fourth frequencies and at the second and fourth frequencies, respectively, wherein a ratio of said third and fourth sideband signals is developed, and wherein an ultimate ratio of the two previously developed ratios is obtained.

4. A method according to claim 1 wherein the amount of one of the first and second gases substantially exceeds the amount of the other, and wherein the path of the serially directed radiant energy includes a filter volume containing only the more prevalent of the first and second gases.

5. A method for determining the relative amounts of first and second gases in an unknown gas mixture, comprising, directing radiant energy serially through a first reference volume of said first gas, a second reference volume of said second gas, a sample volume of the unknown gas mixture, and a third reference volume containing a predetermined ratio of said first and second gases, said radiant energy having a wavelength spectrum including characteristic absorption wavelengths of said first and second gases, modulating the absorption of the radiant energy by the first and second reference volumes, the sample volume, and the third reference volume, detecting the amount of radiant energy passing serially through the first, second, and third reference volumes and the sample volume, and developing signals representative thereof, and processing such signals to derive an output signal representative of the ratio of the ratio of the amounts of the first and second gases in the sample volume to the ratio of the amounts of the first and second gases in the third reference volume.

6. A method according to claim 5 wherein the energy absorption of the first and second reference volumes, the sample volume, and the third reference volume is modulated at first, second, third, and fourth frequencies, respectively, and wherein the signals representing the detected radiant energy are processed by developing first and second corresponding sideband signals resulting from heterodyning of the radiant energy modulated at the first and third frequencies and at the second and third frequencies, respectively, obtaining a first ratio of said first and second sideband signals, developing third and fourth corresponding sideband signals resulting from heterodyning of the radiant energy modulated at the first and fourth frequencies and at the second and fourth frequencies, respectively obtaining a second ratio of said third and fourth sideband signals, and obtaining an ultimate ratio of said first and second ratios.

7. The method of claim 5 wherein one of the first and second gases is carbon dioxide having substantially only carbon 12 atoms and the other of said first and second gases comprises carbon dioxide having substantially only carbon 13 atoms.

8. Apparatus for determining the relative amounts of first and second gases in an unknown gas mixture, comprising, means for containing a first reference volume of the first gas, a second reference volume of the second gas, and a sample volume of the unknown gas mixture, means for directing radiant energy having a wavelength spectrum including characteristic absorption wavelengths of the first and second gases through the first and second reference volumes and the sample volume, means for modulating the absorption of the radiant energy by the first and second reference volumes and the sample volume at first, second and third frequencies, respectively, means for detecting the amount of radiant energy passing serially through the first and second reference volumes and the sample volume, demodulator means for developing first and second corresponding sideband signals in the detected radiant energy arising from the first and third frequencies and arising from the second and third frequencies, respectively, and means for obtaining a ratio of said first and second sideband signals.

9. Apparatus according to claim 8 including means defining a third reference volume for containing a predetermined ratio of the first and second gases positioned in the path of the serially directed radiant energy, means for modulating the absorption of the radiant energy by the third reference volume at a fourth frequency, said demodulator means including means for developing third and fourth corresponding sideband signals in the detected radiant energy arising from the first and fourth frequencies and arising from the second and fourth frequencies, respectively, means for obtaining a ratio of said third and fourth sideband signals, and means for obtaining an ultimate ratio of said previously named sideband signal ratios.

10. Apparatus according to claim 9 wherein said modulating means comprise means for varying the densities of said reference volumes and said sample volume.

11. Apparatus according to claim 9 including interference filter means disposed in the path of the radiation for selecting only that portion of the radiation which includes the characteristic absorption wavelength bands of the two gases of interest.

12. Apparatus for determining the relative amounts of first and second gases in an unknown gas mixture, comprising, a first reference cell for containing a volume of the first reference gas, a second reference cell for containing a volume of the second reference gas, a sample cell for containing the unknown gas mixture, a third reference cell for containing a volume of a mixture of the first and second gases in a predetermined ratio, a source for directing radiant energy serially through said reference cells and said sample cell, means for modulating the density of gases contained in said reference and sample cells, a detector for detecting the amount of radiant energy passing through said reference and sample cells, and signal processing means coupled to said detector for developing an output signal representative of the ratio of the amounts of the first and second gases in said sample cell to the ratio of the amounts of the first and second gases in said third reference cell.

13. Apparatus according to claim 12 wherein said signal processing means include means for developing a first intermediate signal representative of the ratio of the amounts of each of the first and second gases in the sample, means for developing a second intermediate signal representative of the ratio of the amounts of each of the first and second gases in the fourth reference cell, and means for developing an output signal representative of the ratio of the first and second intermediate signals.

14. Apparatus according to claim 13 wherein said means for developing the first intermediate signal comprise a circuit for developing a sideband signal from the sum or difference of the modulation frequencies of the gases in said first and second reference cells and the modulation frequency in said sample cell, and wherein said means for developing the second intermediate signal comprise a circuit for developing a corresponding sideband signal from the sum or difference of the modulation frequencies of the gases in said first and second reference cells and the modulation frequency of the gases in said third reference cell, and means for obtaining a ratio of corresponding sideband signals.

15. Apparatus according to claim 12 wherein said modulating means comprise acoustic drivers.

16. Apparatus according to claim 12 for use wherein the amount of the first and second gases substantially exceeds the amount of the other, including a filter cell positioned to be in the path of the radiant energy for containing a volume of only the more prevalent of the first and second gases.

17. The method of claim 1 wherein the first and second reference volumes are arranged so that radiant energy passes therethrough prior to passing through the sample volume.

18. Apparatus according to claim 8 wherein the first and second reference volumes are arranged between said means for directing radiant energy and said sample volume so that the radiant energy passes through said first and second reference volumes prior to passing through the sample volume.

* * * * *

UNITED STATES PATENT AND TRADEMARK OFFICE
CERTIFICATE OF CORRECTION

PATENT NO. : 4,027,972
DATED : June 7, 1977
INVENTOR(S) : Donald W. Davies

It is certified that error appears in the above-identified patent and that said Letters Patent are hereby corrected as shown below:

Column 2, line 27, change "mixtures" to ---mixture---.

Column 3, line 13, change "interface" to ---interference---.

Column 4, line 8, change "representinhg" to ---representing---

Column 4, line 10, delete "the".

Column 4, line 67, change "signal" to ---signals---.

Column 8, line 51, after "amount" insert ---of one---.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks